(12) United States Patent
Lindén

(10) Patent No.: US 6,749,723 B2
(45) Date of Patent: Jun. 15, 2004

(54) MEASURING ARRANGEMENTS IN A SHORTENED DRY END OF A TISSUE MACHINE

(75) Inventor: Anders Tommy Lindén, Karlstad (SE)

(73) Assignee: Metso Paper Karlstad AB, Karlstad (SE)

( * ) Notice: Subject to any disclaimer, the term of this patent is extended or adjusted under 35 U.S.C. 154(b) by 0 days.

(21) Appl. No.: 10/214,688

(22) Filed: Aug. 8, 2002

(65) Prior Publication Data

US 2002/0189775 A1 Dec. 19, 2002

Related U.S. Application Data

(63) Continuation-in-part of application No. 09/882,659, filed on Jun. 15, 2001, now Pat. No. 6,669,818.
(60) Provisional application No. 60/214,507, filed on Jun. 28, 2000.

(51) Int. Cl.[7] .............................. D21F 5/02; D21F 7/02; D21F 7/06; G01N 21/89
(52) U.S. Cl. .................. 162/198; 162/118; 162/193; 162/207; 162/263; 162/283; 162/381; 34/444; 34/625; 34/659
(58) Field of Search ................ 162/283, 381, 162/109–118, 193, 198, 199, 263, 272, 306, DIG. 6; 34/459, 618, 623, 625, 659, 444–447, 111–123; 226/10, 91, 92, 97.1, 97.3; 700/127–129; 356/429–431; 250/339.1, 339.11, 559.01

(56) References Cited

U.S. PATENT DOCUMENTS

| 1,842,889 | A |   | 1/1932  | Williams |
| 3,732,430 | A |   | 5/1973  | Hujer et al. |
| 4,179,330 | A |   | 12/1979 | Page |
| 4,596,633 | A |   | 6/1986  | Attwood |
| 4,848,633 | A | * | 7/1989  | Hagen et al. ............... 226/97.3 |
| 4,881,327 | A | * | 11/1989 | Hauser et al. ................ 34/114 |
| 4,883,233 | A |   | 11/1989 | Saukkonen et al. |
| 4,921,183 | A |   | 5/1990  | Saukkonen et al. |
| 5,026,458 | A |   | 6/1991  | Beuther |
| 5,130,559 | A | * | 7/1992  | Leifeld et al. ......... 250/559.11 |
| 5,150,850 | A |   | 9/1992  | Adams |
| 5,308,008 | A |   | 5/1994  | Rüegg |
| 5,377,428 | A |   | 1/1995  | Clark |

(List continued on next page.)

FOREIGN PATENT DOCUMENTS

| WO | WO 01/02841    | * | 1/2001 | .......... G01N/22/00 |
| WO | WO 01/06241 A1 |   | 1/2001 | |

OTHER PUBLICATIONS

Copy of PCT International Search Report for PCT Application PCT/SE 03/01243, filed Jul. 28, 2003, Completion Date of Search Report Oct. 7, 2003 (Mailed Oct. 16, 2003).

*Primary Examiner*—Steven P. Griffin
*Assistant Examiner*—Eric Hug
(74) *Attorney, Agent, or Firm*—Alston & Bird LLP

(57) ABSTRACT

A property of a paper web is measured using one or more reflectance measurement sensors emitting measuring beams onto the web and receiving the beams reflected from the web, from which the web property is deduced. The web is supported on a web support during the measurement, such as on a passive or active airfoil or fabric. One or more measurement sensor(s) can be integrated within an active airfoil, and can comprise a plurality of optical fibers having sensing ends arranged in the airfoil such that the sensing ends of the fibers face the moving paper web through one or more apertures in a web-supporting panel of the airfoil. Alternatively, a traversing sensor can be mounted within the airfoil. Other embodiments include a reflectance sensor mounted adjacent an airfoil or other web support such as a through-air drying fabric or a support belt for the web.

27 Claims, 7 Drawing Sheets

U.S. PATENT DOCUMENTS

| | | |
|---|---|---|
| 5,377,931 A | 1/1995 | Dörfel et al. |
| 5,400,707 A | 3/1995 | Neider et al. |
| 5,544,841 A | 8/1996 | Didier et al. |
| 5,593,545 A | 1/1997 | Rugowski et al. |
| 5,891,309 A | 4/1999 | Page et al. |
| 5,895,007 A | 4/1999 | Moller et al. |
| 5,918,830 A | 7/1999 | Verajankorva et al. |
| 5,931,406 A | 8/1999 | Siebert |
| 5,944,273 A | 8/1999 | Lin et al. |
| 5,954,291 A | 9/1999 | Meinecke et al. |
| 6,183,601 B1 | 2/2001 | Otto et al. |
| 6,193,845 B1 * | 2/2001 | Graf et al. ................ 162/193 |
| 6,196,492 B1 | 3/2001 | Baumeister |
| 6,254,726 B1 * | 7/2001 | Steiner et al. ............. 162/198 |
| 6,398,916 B1 | 6/2002 | Klerelid |
| 6,447,640 B1 | 9/2002 | Watson et al. |
| 6,490,813 B1 * | 12/2002 | Oechsle ...................... 34/445 |
| 2002/0060036 A1 | 5/2002 | Linden |
| 2003/0075293 A1 * | 4/2003 | Moeller et al. ............. 162/193 |

* cited by examiner

MEASURING ARRANGEMENTS IN A SHORTENED DRY END OF A TISSUE MACHINE

CROSS-REFERENCE TO RELATED APPLICATION

The present invention is a continuation-in-part of U.S. patent application Ser. No. 09/882,659, now U.S. Pat. No. 6,669,818, filed Jun. 15, 2001, which claims the benefit of the filing date of U.S. Provisional Patent Application No. 60/214,507, filed Jun. 28, 2000, the disclosure of which is incorporated herein by reference.

FIELD OF THE INVENTION

The invention relates to papermaking machinery and methods. The invention relates more particularly to measuring arrangements for measuring properties of a moving paper web in a shortened dry end of a tissue machine.

BACKGROUND OF THE INVENTION

In the production of paper, it is common practice to monitor the condition of the paper web at certain points along the web's passage through the papermaking machine, and to adjust the papermaking process as necessary depending on the condition of the web. For instance, in the dry end of a paper machine, the web exiting from the final drying section of the machine is typically monitored to measure properties such as the basis weight and moisture. In particular, the profiles of such properties in the machine direction (MD) and cross-machine direction (CD) are deduced from the measurements. An ideal web would have flat MD and CD profiles of all parameters of interest. In the real world, such profiles are never flat at all times. Through monitoring of the profiles and appropriate adjustment of the papermaking process in a closed-loop control, however, the profiles can be maintained close to the desired flat state.

Various types of sensor devices have been used for monitoring the properties of a moving paper web. The sensor devices typically comprise optical sensors employing light transmission through the web and/or reflection from the web, and detection of the transmitted or reflected light, from which paper properties of interest are deduced. With most types of sensors, it has been the conventional practice to mount the sensors on a measuring frame whose only or primary purpose is to support the sensors. For example, in a conventional tissue machine employing a final Yankee dryer, a measuring frame located just downstream of the Yankee dryer and upstream of the reel-up supports sensors for measuring basis weight and moisture content of the finally dried web.

In some paper machines, the sensors are traversed in the cross-machine direction. The direction of traverse is normally substantially perpendicular to the direction of movement of the web. The sensors therefore measure properties of diagonal samples of the web, rather than the whole web. Measurements are made at substantially the same plurality of locations across the machine during each traverse, and they may be made while traversing the sensors in one or both directions across the web. Measured variations in web properties of interest are commonly separated by means of numerical algorithms into estimates of the MD and CD variations. The usual separation methods attempt to identify MD variations and to separate them from the scan data, and the remaining variations are considered to be CD and random variations. MD variations of high frequency cannot be separated and are commonly deemed to be random variations. Variations designated as random are often removed by filtering. MD variations of low frequency may be substantially identified and separated with any of several numerical algorithms. Such algorithms include averaging, exponential filtering, or Kalman filtering applied to each cell.

A drawback of the conventional arrangement is that the measuring frame takes up space in the machine direction and, consequently, the draw between the Yankee dryer or other final dryer and the reel-up becomes somewhat long. As a further consequence of this long draw, the paper web must be supported between the final dryer and reel-up, or else the web will not be stable and will not be capable of supporting its own weight without risk of breaking. Thus, sophisticated supporting equipment is required.

Traversing sensors also tend to collect fibers and debris and hence must be regularly cleaned to maintain their proper operation and to prevent dust accumulation that can present a fire hazard.

Still another disadvantage of typical measuring arrangements is that basis weight is measured by placing a source of radioactive isotopes on one side of the web and a detector on the other side of the web. The detector receives the radioactive rays after their passage through the web and deduces basis weight based on the degree to which the web absorbs the radiation. Not only are radioactive emissions potentially hazardous to personnel, but the through-web transmission technique requires that the web traverse an open draw in the region of the measuring arrangement. In tissue machines, this is disadvantageous because the tissue web is weak and hence can tend to break in open draws.

SUMMARY OF THE INVENTION

The present invention seeks to address the above-noted needs, by providing measuring arrangements that facilitate shortening of the dry end of a tissue machine and that allow paper properties to be measured without the requirement of an open draw. In accordance with the invention, the paper web is measured for basis weight and other parameters while supported on a fabric or other web support. To this end, a reflectance measurement technique is used in which measuring beams (e.g., electromagnetic waves, acoustic waves such as ultrasonic energy, light waves in the visible or invisible spectrum, or the like) are emitted onto the web on the web support and are reflected from the web back to a sensor. Thus, no open draw is required because the sensors that emit and receive the beams are located on only one side of the web.

In some aspects of the invention, traversing sensors are eliminated in favor of fixed sensors that are not subject to the problems associated with traversing sensors. In other aspects of the invention, traversing sensors are used but they are housed in such a way that they are not susceptible to being fouled with dust or other debris, and a measuring frame is not required for supporting the sensors.

Thus, one aspect of the invention provides an active airfoil for a papermaking machine with a fiber optic measuring device integrated into the airfoil. The active airfoil generally comprises a panel defining a web-supporting surface and a plurality of other walls joined to the panel so as to form an internal chamber that is supplied with air under pressure. The airfoil defines one or more air outlets that discharge air from the chamber and along the web-supporting surface to form an air layer that supports a moving paper web traveling along the web-supporting surface. The fiber optic measuring device comprises a plurality of optical fibers having sensing ends. The optical fibers are arranged in the airfoil such that the sensing ends of the fibers face the moving paper web through one or more apertures in the web-supporting panel of the airfoil. The sensing ends of the fibers are spaced apart in the cross-machine direction so that paper properties can be sensed at a plurality of widthwise locations along the web. The optical sensors preferably employ a reflectance measurement technique in which light waves are emitted from ends of some of the optical fibers and reflected waves are received by ends of others of the optical fibers.

In accordance with a preferred embodiment of the invention, the opposite ends of the optical fibers are connected to a sampling device located remote from the airfoil. The sampling device sequentially samples the optical output signals from the optical fibers, and provides samples of the signals to a further device such as a computer, which can determine the web MD and CD profiles therefrom. The sampling device is capable of sampling all of the optical fibers across the entire width of the web much faster than a traversing sensor can be moved across the width, thereby enabling high- and low-frequency MD variations to be detected. The sampling device can be a mechanical device such as a rotating device that is rotated to be coupled sequentially with the ends of the optical fibers arranged about a circular path; alternatively, the sampling device can accomplish the sampling electronically.

In another embodiment of the invention, an active airfoil houses a traversing sensor that performs reflectance measurements by emitting and receiving through one or more openings in the web-supporting wall of the airfoil. The traversing mechanism is shielded by the airfoil from dust and other debris that can foul conventionally mounted traversing sensors.

It is also possible in accordance with the invention to support the web on an active airfoil, passive airfoil, fabric, or other web support and to mount reflectance measurement sensors adjacent the exposed side of the web on the web support.

In one embodiment of the invention, an active airfoil, whether or not it houses sensors, preferably supports the web from the final drying device up to the reel-up in a tissue machine so that there is no open draw, or at most a very short open draw between the airfoil and the reel-up. When the active airfoil is coupled with reflectance sensors mounted either within or adjacent the airfoil, a particularly compact dry end is provided.

More particularly, an apparatus for a dry end of a tissue machine includes a rotatable reel spool onto which the paper web is wound to form a paper roll, and an active airfoil extending from the dryer to the paper roll. The active airfoil in some embodiments has a downstream edge that forms a nip with the paper roll through which the paper web is guided onto the paper roll. In other embodiments, the airfoil does not form a nip with the paper roll, in which case there can be a very short free draw between the downstream edge of the airfoil and the paper roll. Where the active airfoil forms a nip with the paper roll, the active airfoil can be movable relative to the reel spool for controlling the nip load in the nip. Advantageously, the active airfoil can be rotatable about a pivot axis for controlling the nip load. Alternatively or additionally, the active airfoil can include a downstream edge portion that is flexible and bears against the paper roll to form the nip.

As an alternative to supporting the web on an airfoil, the web can be supported on a belt or fabric that extends up to the reel-up. In this case, the reflectance measuring sensors are mounted on a suitable support adjacent the belt or fabric. The web is positioned between the sensors and the belt or fabric.

The invention enables a number of advantages to be achieved over conventional paper machines. The airfoil with integrated fiber optic measuring device requires no traversing measuring head, and hence complicated traversing mechanisms and the vibrations and cleaning problems that are associated with such measuring heads are eliminated. Integration of the measuring device into the active airfoil rather than on a separate measuring frame or the like also saves space and reduces the footprint of the machine. The optical fibers can be routed internally within the active airfoil, and thus will not cause a dust accumulation that could be a fire hazard. Additionally, MD variations are easily detectable by monitoring each sensor at a given widthwise position along the web with a high frequency or even continuously.

When the reflectance measurement sensors are not integrated into an active airfoil, they can be mounted wherever there is a direct line of sight to the paper web supported on a support such as a fabric or airfoil. For example, the sensors can be mounted adjacent a through-air drying fabric on which the web is carried in the drying section, at a location where the paper web is carried on an outward-facing surface of the fabric such that there is a line of sight to the web. The invention thus enables substantial freedom in placement of the sensors.

BRIEF DESCRIPTION OF THE DRAWINGS

The above and other objects, features, and advantages of the invention will become more apparent from the following description of certain preferred embodiments thereof, when taken in conjunction with the accompanying drawings in which:

FIG. 2A is a fragmentary plan view of the active airfoil as viewed along line 2A—2A in FIG. 2;

DETAILED DESCRIPTION OF THE DRAWINGS

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
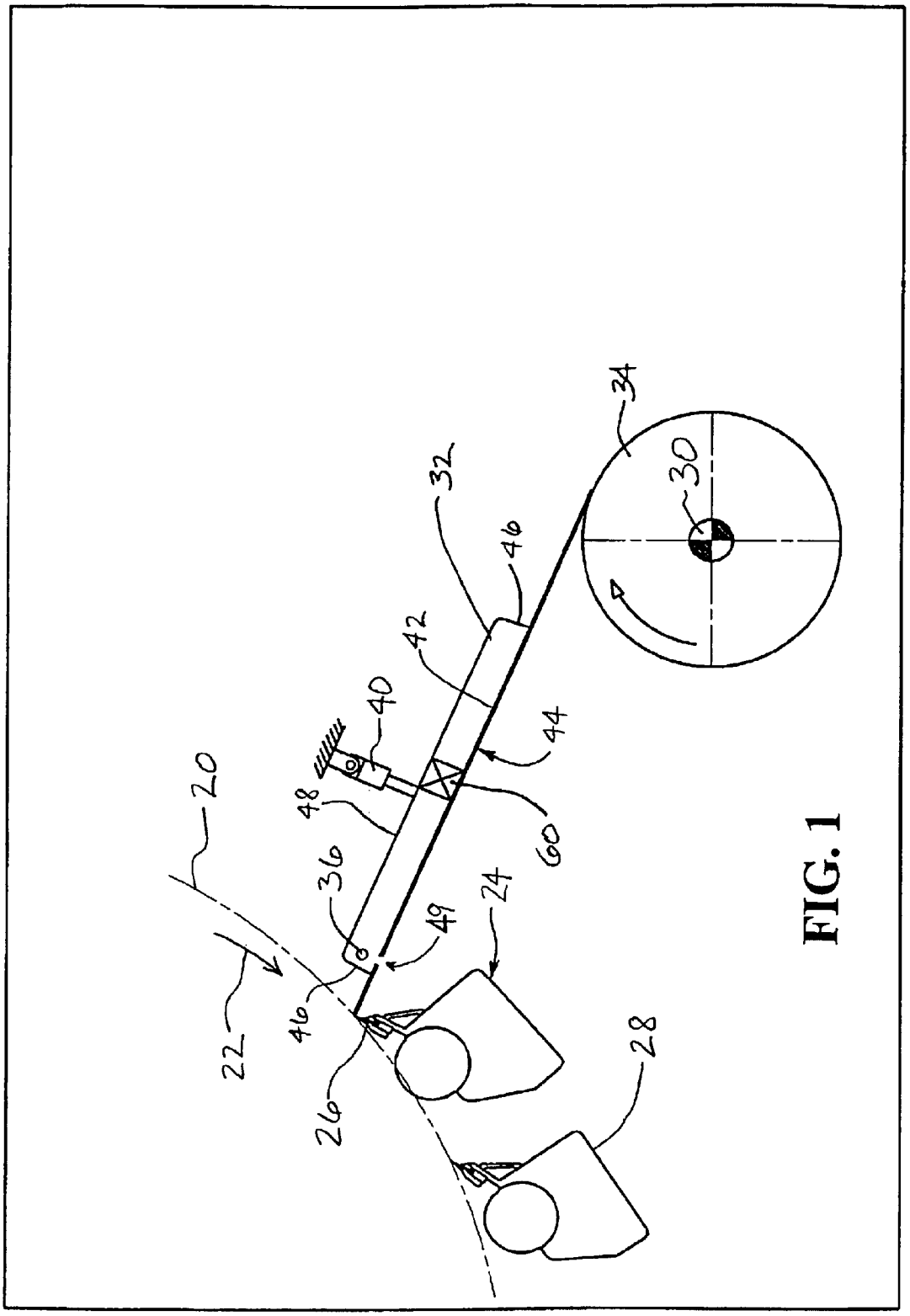
FIG. 1 is a diagrammatic depiction of a dry end of a paper machine in accordance with one embodiment of the invention having a driven reel spool closely coupled to the creping doctor with a pivotable active airfoil therebetween, with the reel spool in a lower position relative to the airfoil.

FIG. 1 depicts the dry end of a papermaking machine in accordance with a first embodiment of the invention, suitable for making tissue. The paper web, as is conventional, is dried on a Yankee dryer having a heated dryer roll 20 rotating in the direction of arrow 22. The web is removed from the roll 20 and preferably creped by a creping doctor 24 having a doctor blade 26. A cleaning doctor 28 arranged after the creping doctor cleans the surface of the roll. Alternatively, the doctor 28 can be used for removing and creping the paper web from the roll 20 when the doctor 26 is out of service for replacement or maintenance. The web creped from the dryer roll 20 proceeds over a short draw to a driven reel spool 30 rotating in the same direction as that of the dryer roll 20. In the draw between the creping doctor 24 and the reel spool 30, the web is stabilized by an active airfoil 32 having its upstream edge adjacent the creping doctor blade 26 and its downstream edge proximate the paper roll 34 building on the reel spool 30. The airfoil 32 advantageously extends across the full width of the paper web in the cross-machine direction. The airfoil 32 is mounted so as to be rotatable about a pivot axis 36 located near the upstream edge of the airfoil and extending parallel to the cross-machine direction. Thus, the airfoil can be pivoted to keep the downstream edge of the airfoil in a desired position relative to the growing paper roll 34. An actuator 40 provides the actuation force pivoting the airfoil 32 as the paper roll grows. The airfoil 32 acts to suppress flutter of the web, which can occur particularly with webs of low basis weight traveling at high speeds.

The airfoil comprises an active airfoil that uses pressurized air to create a directed air flow for supporting and assisting the web's movement. Such an active airfoil is described, for example, in U.S. Pat. No. 5,738,760, the disclosure of which is incorporated herein by reference. Briefly, the airfoil has a panel 42 defining a web-supporting surface 44 along which the paper web travels, and a plurality of other walls 46, 48 that, together with the panel 42, define an internal chamber into which pressurized air is supplied. Openings 49 in the panel 42 discharge air from the chamber in a direction generally parallel to the web-supporting surface 44 of the panel, thus creating a layer of moving air that supports the paper web.

Figure 2:
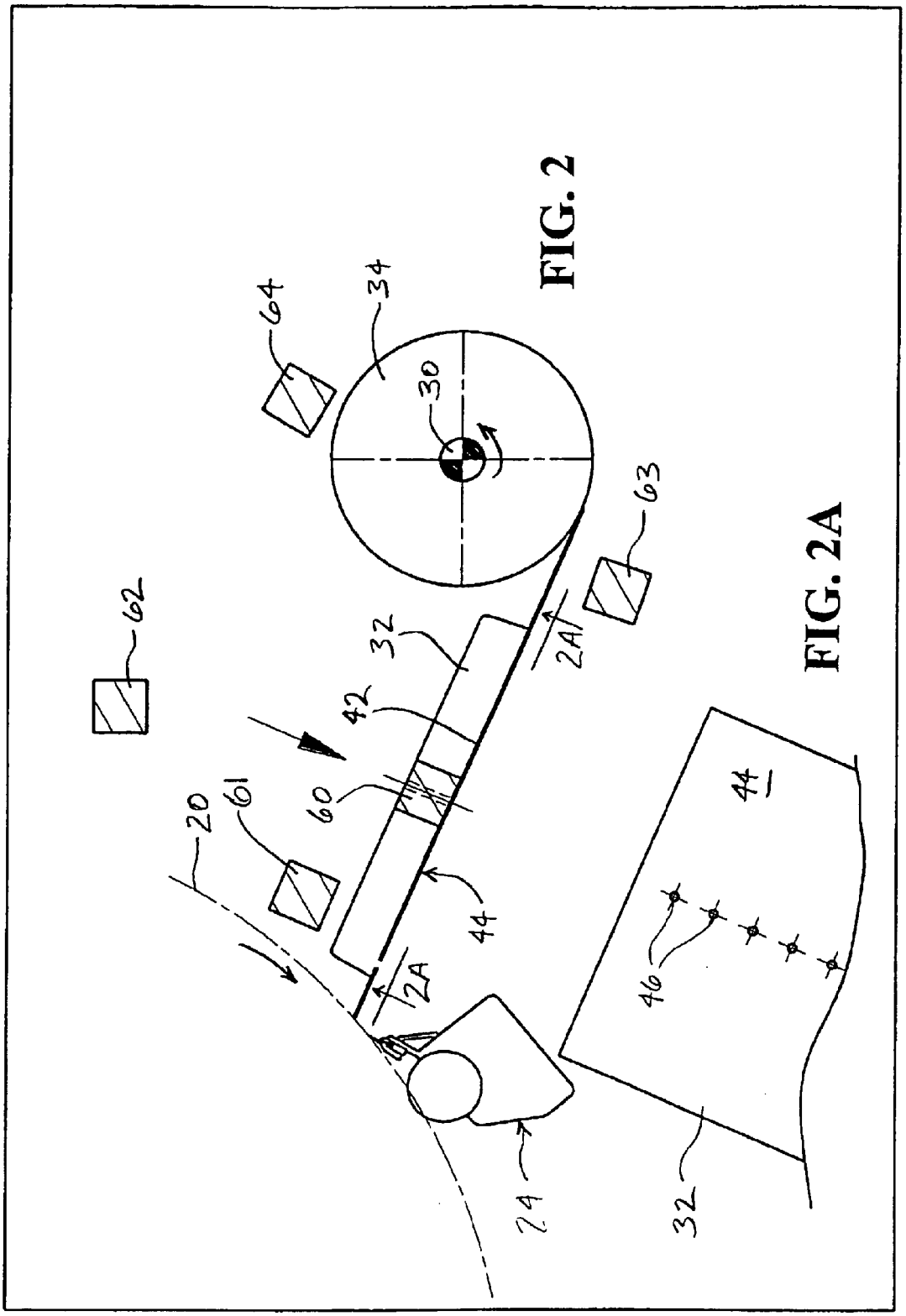
FIG. 2 is a view similar to FIG. 1, but with the reel spool in an upper position relative to the airfoil.

FIG. 2 shows an alternative embodiment of the invention, which is similar to that of FIG. 1 except that the reel spool 30 is arranged in an upper position relative to the active airfoil 32 so that the paper web is wound onto a lower side of the building paper roll 34, which rotates in a opposite direction to that of the Yankee dryer 20.

The airfoil 32 also includes an integrated fiber optic measuring device 60. The fiber optic measuring device 60 comprises a plurality of optical fibers 62, shown schematically in FIG. 3, that are routed along the airfoil 32 either internally in the airfoil or along an outer surface other than the web-supporting surface 44. Each optical fiber 62 has a sensing end for receiving light and transmitting the light along the fiber to an opposite end thereof where the transmitted light is detected and properties of the paper web are deduced therefrom. The sensing ends of the fibers 62 face the paper web traveling along the web-supporting surface 44 of the airfoil. To this end, the panel 42 of the airfoil includes a plurality of apertures 46 therethrough, and the ends of the optical fibers 62 are received in these apertures so that the sensing ends of the fibers are substantially flush with the web-supporting surface. Alternatively, the sensing ends of the fibers can be recessed below the web-supporting surface 44; it is also possible in this case to cover the apertures 46 with a transparent cover (not shown) of glass or plastic, for example, to prevent the optical fibers from being fouled by fibers or debris, the cover being arranged to be flush with the web-supporting surface 44. It is further possible to employ a slot-shaped aperture (or more than one such aperture) in the airfoil panel 42 and to arrange a plurality of optical fibers in a single aperture, as opposed to having a separate aperture for each fiber.

Regardless of how the fibers 62 and aperture(s) 46 are arranged, the sensing ends of the fibers are spaced apart along the cross-machine direction, as shown in FIG. 2A. The fiber ends are spaced across substantially the entire width, or over only a portion of the width, of the paper web at predetermined intervals, e.g., about 50–150 mm, and preferably about 100 mm. Although the fiber ends are shown in FIG. 2A as being arranged in a straight row and with uniform spacing, the invention is not limited to any particular configuration and placement of the fiber ends; alternative placements can be used depending on which portions of the paper web are to be monitored.

Figure 3:
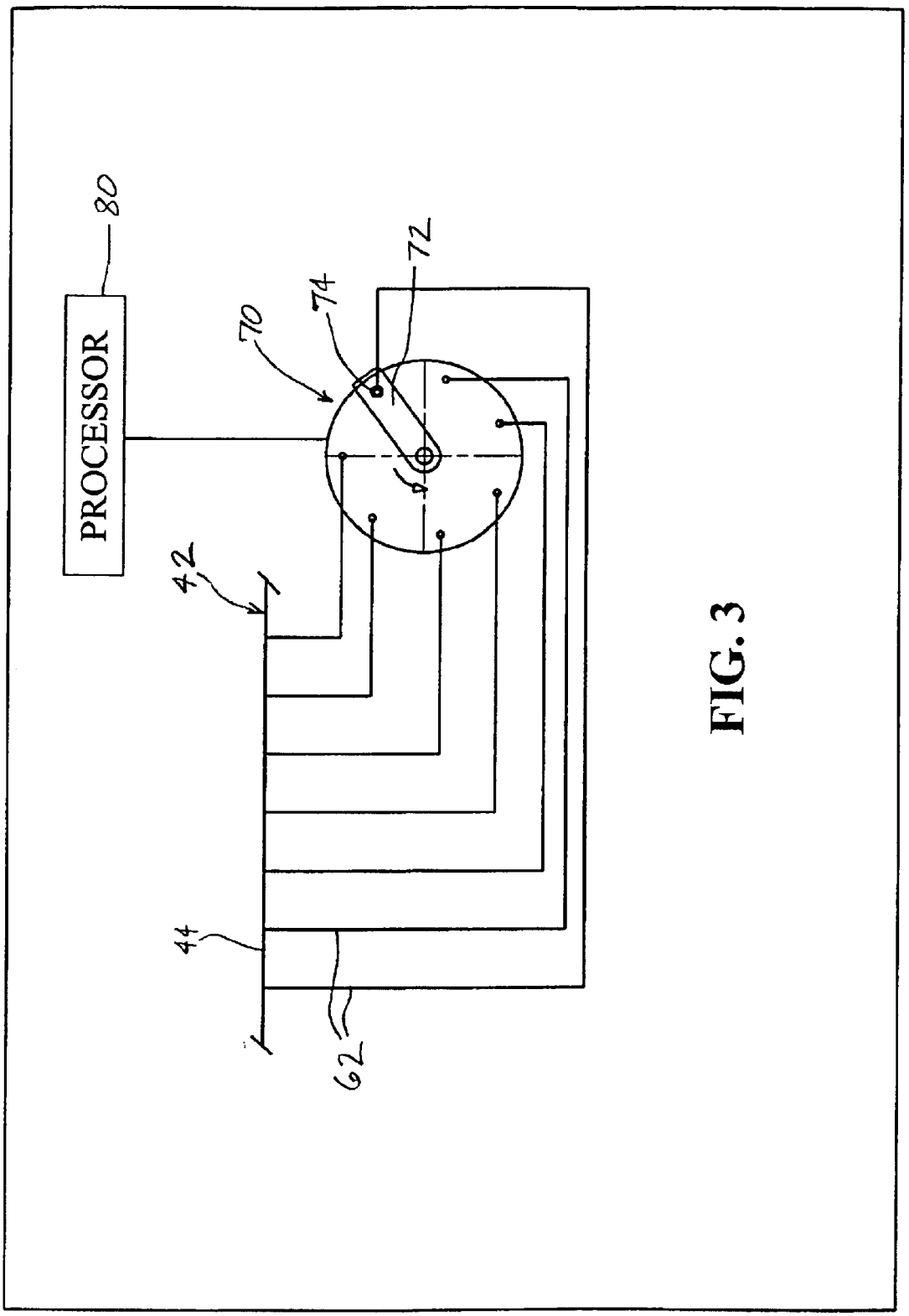
FIG. 3 is a schematic depiction of a sampling device connected to the optical fibers of the airfoil.

FIG. 3 shows a sampling device 70 that receives the opposite ends of the optical fibers 62 and detects the light transmitted by each fiber. While the light transmitted by each fiber may be continuous, the sampling device may only periodically detect the light transmitted by any particular fiber. Thus, for example, the sampling device may be a mechanical device such as the rotary device shown in FIG. 3, in which a member 72 carrying a detector 74 revolves such that the detector 74 is brought into alignment with the end of each optical fiber 62 in turn. Each optical fiber thus is sampled once per revolution of the member 72. The signal sampled from each fiber is then communicated to a processor 80 such as a programmed computer, which is operable to deduce properties of the paper web from the signals. The sampling device 70 can send signals to the processor 80 as optical signals over a fiber optic cable, in which case the processor 80 is operable to convert the optical signals to electrical signals that are then quantified and used in calculating properties of the paper web. Alternatively, the sampling device can convert the optical signals from the fibers into electrical signals and can send the converted electrical signals to the processor.

Although a rotary sampling device is shown, alternatively a linearly moving sampling device could be used. It is also possible to employ a sampling device that samples the fiber optic signals by electronic sampling rather than mechanical sampling. It will also be recognized that the sampling device and processor could be integrated into the same device, if desired. Furthermore, each optical fiber could have its own dedicated device continuously converting the optical signal into electrical signals so that all optical signals of all fibers are simultaneously converted into electrical signals that are either continuously or periodically monitored.

As shown in FIG. 2, in addition to the fiber optic measuring device 60, the dry end of the paper machine can also include further sensors 61–64 in various locations for measuring web properties. Advantageously, the sensor 61 can comprise an infrared temperature sensor placed upstream of the creping doctor 24 for measuring web temperature prior to the web being creped from the dryer roll 20. It has been found that there is a good correlation between web moisture content and the web temperature measured by an infrared temperature sensor. Accordingly, the web temperature measured by the sensor 61 can be used for determining web moisture content going into the dry end. Sensors 63 and 64 can be used for measuring the speed of the web.

The sensors 60 measure paper properties preferably using a reflectance technique. Measuring beams such as electromagnetic waves, ultrasonic energy, light waves in the visible or invisible spectrum, or the like, are emitted by the sensors onto the web passing along the airfoil, and reflected measuring beams from the web are received by the sensors and processed to deduce web properties. In particular, the moisture content and/or basis weight of the paper preferably are determined. Moisture content of the web can be measured using infrared sensors and techniques; such techniques are known.

Prior to the invention, the measurement of basis weight has been carried out by placing a source of radioactive isotopes on one side of the web and a detector on the other side. The detector receives the radioactive rays that pass through the web and deduces basis weight based on the amount of absorption of the radioactivity by the web. In accordance with the invention, however, measuring beams such as infrared waves are reflected from the web and the reflected measuring beams are received and analyzed using spectral analysis methods. Basis weight is correlated with changes in the spectral content of the reflected measuring beams, such that based on the spectral analysis the basis weight of the paper is deduced.

Figure 4:
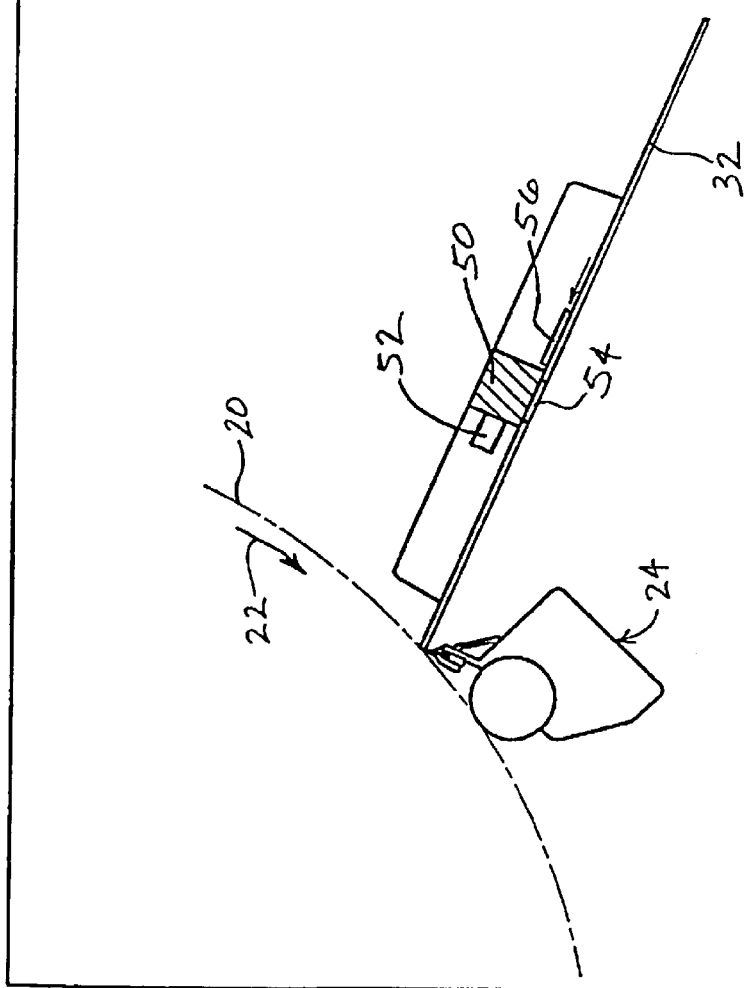
FIG. 4 depicts an active airfoil housing a traversing sensor in accordance with another embodiment of the invention.

The invention is not limited to fixed sensors. FIG. 4 depicts an embodiment of an active airfoil 32 having a measuring head 50 housed within it. The measuring head 50 comprises at least one sensor for measuring one or more properties of the paper web such as basis weight. The head 50 can incorporate more than one sensor, such as a basis weight sensor and a moisture or temperature sensor. Advantageously, the measuring head 50 is traversable in the cross-machine direction along a rail 52 or the like. The airfoil includes a slot 54 extending along the cross-machine direction aligned with the traversing head 50. The airfoil can include a movable cover 56 for covering the slot 54 when the measuring head 50 is not being used to measure the web property or properties. The sensors of the measuring head 50 preferably employ a reflectance measurement technique as described previously.

Figure 5:
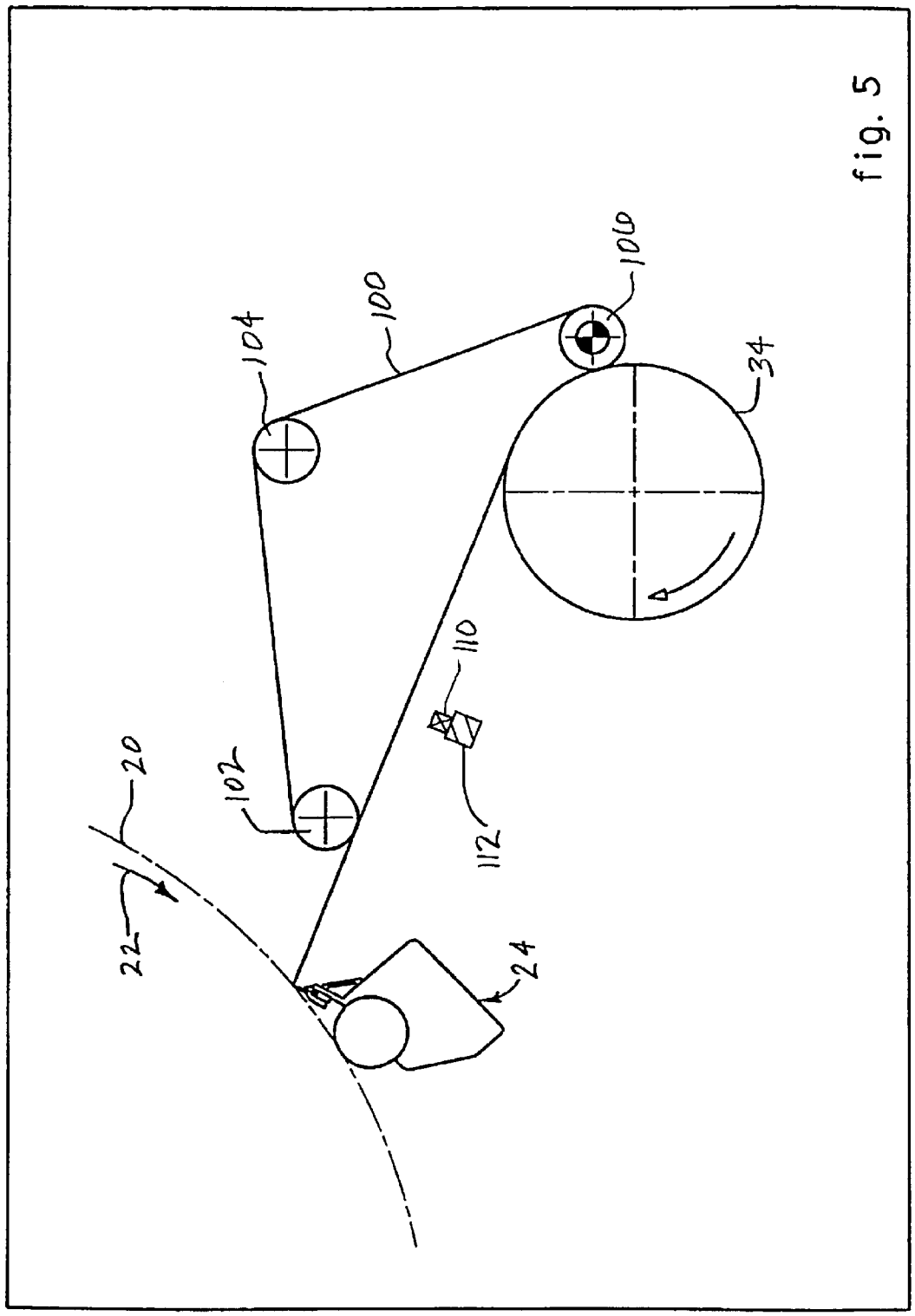
FIG. 5 illustrates a dry end in accordance with a further embodiment of the invention, in which a web support in the form of a belt carries the web to the reel-up, and reflectance measurement sensors are mounted adjacent the belt.
Figure 6:
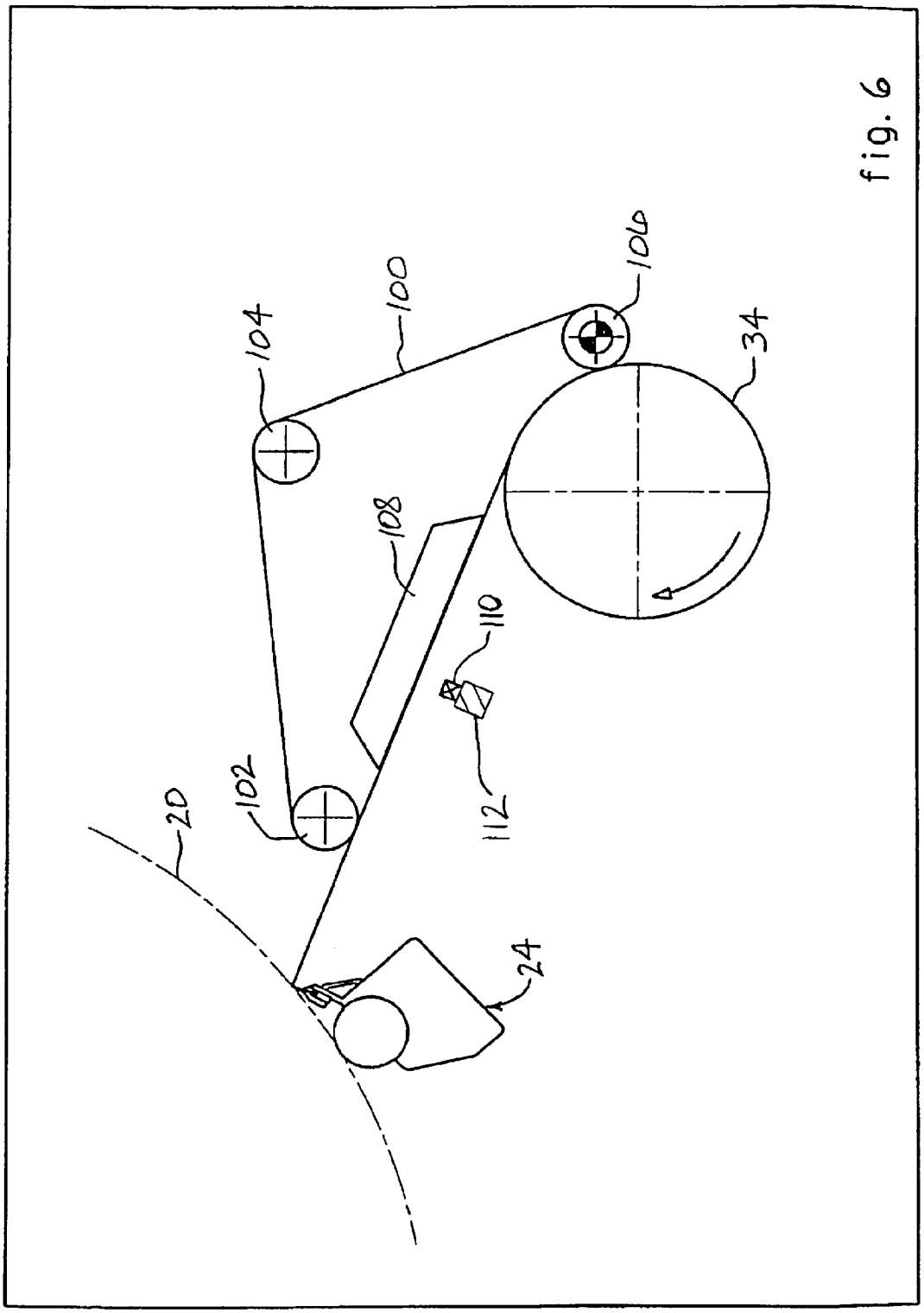
FIG. 6 shows an embodiment similar to that of FIG. 5, with the addition of a device for creating an underpressure disposed on the opposite side of the belt from the web.

FIG. 5 depicts yet another embodiment of the invention in which the reel-up includes a belt 100 looped about a plurality of guide rolls 102, 104, and 106, the guide roll 106 being rotatably driven for driving the belt. The guide roll 106 is located adjacent the building paper roll 34. The guide roll 102 is spaced upstream from the paper roll 34 and a short distance downstream from the creping doctor 24. The portion of the loop of the belt between the guide roll 102 and the guide roll 106 acts to stabilize the web as it travels from the creping doctor to the nip defined between the belt 100 and the paper roll 34. FIG. 6 shows a variant in which a device 108 for creating an underpressure is disposed within the loop of the belt 100; in this embodiment, the belt 100 should be permeable. The device 108 can be a vacuum box, or alternatively can be a device that creates an underpressure by blowing air via the Coanda effect, such as a device marketed by Metso Corporation under the trademark Blowbox.

In the embodiments of FIGS. 5 and 6, reflectance measuring sensors 110 are mounted on a suitable support 112 such as a beam or the like adjacent the support belt 100 such that the web is disposed between the sensors and the belt. The sensors 110 can be either stationary or traversing sensors. The sensors employ the previously described reflectance techniques to measure basis weight, and can also measure one or more other parameters such as moisture content.

The belt 100 in FIGS. 5 and 6 is in an upper position with respect to the web and paper roll, but could alternatively be in a lower position relative to the web and paper roll such that the web is supported atop the belt and is guided by the belt onto a lower side of the paper roll, which rotates counterclockwise (i.e., opposite to the direction shown in FIGS. 5 and 6).

Figure 7:
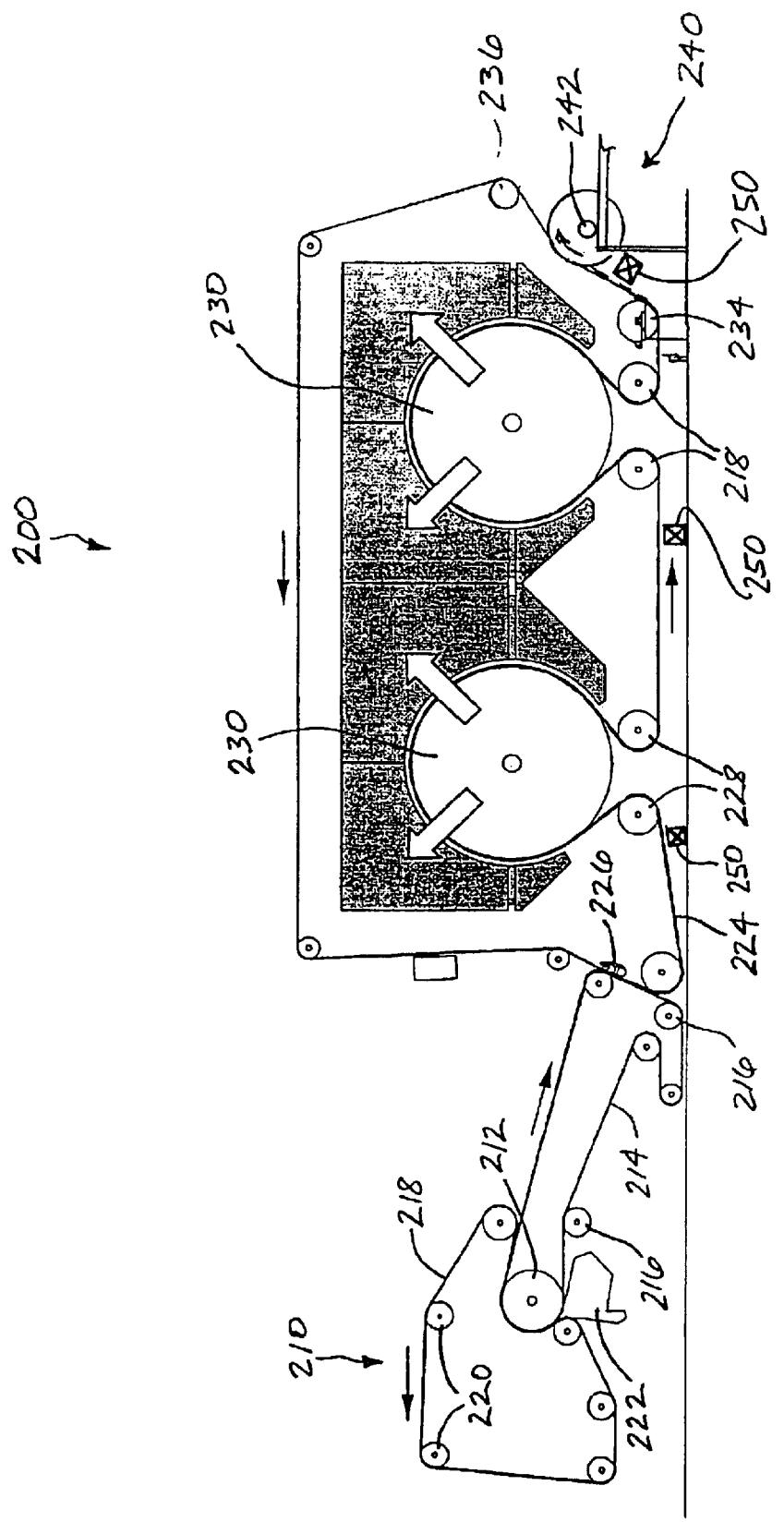
FIG. 7 is a diagrammatic representation of a paper machine in accordance with still another embodiment of the invention having through-air dryers through which the web is carried on a through-air drying fabric, and having reflectance measurement sensors disposed adjacent the fabric for measuring the web thereon.

It will be appreciated by persons skilled in the art that the principles of the invention are not limited to being applied in paper machines employing a Yankee dryer as the final dryer device, but can also be applied in other types of machines such as those employing one or more through-air dryer (TAD) units as the final dryer(s). As but one example, FIG. 7 shows a paper machine 200 in accordance with a preferred embodiment. The machine 200 includes a forming section 210 having a twin-wire former. The former includes a forming roll 212, an inner wire 214 formed in an endless loop about guide rolls 216 such that the inner wire passes about a sector of the forming roll, an outer wire 218 formed in an endless loop about guide rolls 220 such that the outer wire passes about the sector of the forming roll on top of the inner wire, and a head box 222 that discharges an aqueous suspension of papermaking fibers between the inner and outer wires just upstream of the forming roll so as to form a wet paper web between the wires. The wet web is partially dewatered by being pressed between the wires as they pass about the forming roll, and the partially dewatered web is separated from the outer wire and is carried on the inner wire 214 downstream of the forming roll to a web transfer point. At the web transfer point, the web is transferred from the inner wire 214 onto a TAD fabric 224 with the aid of a suction device 226 disposed inside the loop of the TAD fabric. The TAD fabric 224 travels in an endless loop about guide rolls 228. The TAD fabric carrying the web thereon passes about a foraminous dryer roll 230 of each of a pair of outward-flow TAD units. An exhaust hood 232 surrounds the portion of each dryer roll 230 about which the TAD fabric and web pass. In conventional fashion, drying air is supplied from the interior of each dryer roll 230 radially outward through the foraminous mantle of the roll and thus through the web and TAD fabric, and is exhausted by the exhaust hoods.

The TAD fabric downstream of the second TAD unit carries the web on the outward-facing surface of the fabric. The fabric in this location extends between a pair of guide rolls 234, 236 that are disposed respectively upstream and downstream of a winding station of a reel-up 240. The reel-up includes appropriate equipment (not shown) operable to grip and rotatably drive a reel spool 242 about which the paper web is to be wound, and operable to urge the rotatably driven reel spool against the TAD fabric 224 so as to form a nip therebetween. The paper web carried on the TAD fabric passes into this nip and is thus wound onto the reel spool to build a paper roll. The reel-up is operable to move the reel spool as the paper roll builds so as to compensate for the increasing diameter of the roll. It will be appreciated that the paper machine according to FIG. 7 offers a number of advantages. First, the paper web is supported at all times on a wire or fabric, such that there are no free draws. Second, the overall length and footprint of the machine can be made small because the reel-up 240 can be close-coupled to the last TAD unit.

In accordance with the invention, reflectance measuring sensors 250 can be placed at any or all of the positions indicated in FIG. 7 for measuring properties of the paper web supported on the lower surface of the TAD fabric 224. In this manner, the paper web properties are measured without requiring any open draw as in conventional transmission-type measurement methods. The sensors 250 can be either stationary or traversing sensors.

The invention enables a number of advantages to be achieved over conventional paper machines. The reflectance measurement of paper basis weight and other parameters enables open draws to be eliminated and close-coupling of the reel-up to the drying section, thereby lessening the likelihood of web breaks as well as reducing overall machine length and providing a compact arrangement. With respect to the embodiments employing the active airfoil with fiber optic measuring device, the device requires no traversing measuring head, and hence complicated traversing mechanisms and the vibrations and cleaning problems that are associated with such measuring heads are eliminated. Integration of the measuring device into the active airfoil rather than on a separate measuring frame or the like also saves space and reduces the footprint of the machine. The optical fibers can be routed internally within the active airfoil, and thus will not cause a dust accumulation that could be a fire hazard.

Furthermore, the invention makes it relatively easy to detect both high- and low-frequency MD variations in web properties, because the optical fiber signals can be sampled at a rate faster than the shortest expected period of MD variations, or can even be continuously monitored if desired.

Many modifications and other embodiments of the invention will come to mind to one skilled in the art to which this invention pertains having the benefit of the teachings presented in the foregoing descriptions and the associated drawings. For example, the embodiments illustrated and described herein as having a Yankee dryer could instead have other types of drying devices such as through-air dryers. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An apparatus for a papermaking machine, the apparatus comprising:
    an active airfoil having a wall defining a web-supporting surface adjacent to which a paper web travels in the papermaking machine, the wall defining openings through which air is discharged to form an air layer along the web-supporting surface for supporting and stabilizing the paper web; and
    a plurality of fixed sensors integrated into the active airfoil and directed from the web-supporting surface onto the paper web for measuring at least one property of the paper web at each of a plurality of locations spaced along the paper web, the sensors being operable to measure the web property from only one side of the web.

2. The apparatus of claim 1, wherein the fixed sensors comprise a fiber optic measuring device having a plurality of optical fibers each having a sensing end, the sensing ends of the optical fibers facing the paper web traveling over the web-supporting surface.

3. The apparatus of claim 2, wherein the sensing ends of the optical fibers are arranged in one or more apertures formed through the web-supporting surface of the active airfoil.

4. The apparatus of claim 2, wherein the sensing ends of the optical fibers are spaced apart in a cross-machine direction for measuring properties of the paper web at different widthwise positions thereof.

5. The apparatus of claim 2, further comprising a device arranged at opposite ends of the optical fibers from the sensing ends, the device being operable to detect optical signals transmitted by each optical fiber.

6. The apparatus of claim 5, wherein the device comprises a sampling device operable to sequentially sample the optical signals of the optical fibers.

7. The apparatus of claim 6, wherein the sampling device includes a member carrying a detector, the member being movable to place the detector in coupled relation with said opposite end of any one of the optical fibers.

8. The apparatus of claim 7, wherein the member carrying the detector is rotatable.

9. The apparatus of claim 5, further comprising a processor connected to the device so as to receive signals from the device representing samples of the optical signals from the optical fibers, the processor being operable to deduce properties of the paper web from said signals received from the device.

10. The apparatus of claim 2, wherein the fiber optic measuring device comprises a reflectance measuring device for measuring basis weight of the web.

11. A dry end of a papermaking machine, the dry end comprising:
    a dryer for drying a paper web;
    a rotatably driven reel spool for winding the paper web thereon located downstream of the dryer;
    an active airfoil disposed between the dryer and the reel spool, the airfoil having a wall defining a web-supporting surface adjacent to which a paper web travels in the papermaking machine, the wall defining openings through which air is discharged to form an air layer along the web-supporting surface for supporting and stabilizing the paper web; and
    a measuring device integrated into the active airfoil and directed from the web-supporting surface onto the paper web for measuring at least one property of the paper web, the measuring device being operable to measure the property from only one side of the web.

12. The dry end of claim 11, wherein the measuring device comprises a fiber optic measuring device.

13. The dry end of claim 12, wherein the fiber optic measuring device comprises a plurality of optical fibers each having a sensing end, the sensing ends of the optical fibers facing the paper web traveling over the web-supporting surface.

14. The dry end of claim 11, wherein the measuring device comprises a traversing measuring head housed within the active airfoil and operable to travel along a cross-machine direction for measuring the web across the width thereof.

15. The dry end of claim 11, wherein the airfoil has an upstream end adjacent the dryer and a downstream end proximate the reel spool.

16. An apparatus for a papermaking machine, the apparatus comprising:
    an active airfoil having a wall defining a web-supporting surface adjacent to which a paper web travels in the papermaking machine and a plurality of additional walls joined thereto so as to create an enclosure defining an interior into which air is supplied under pressure, the wall having the web-supporting surface defining openings through which air is discharged to form an air layer along the web-supporting surface for supporting and stabilizing the paper web; and a traversing measuring device housed in the interior of the active airfoil for measuring at least one property of the paper web, the measuring device being traversable along a cross-machine direction within the airfoil, the wall of the airfoil having the web-supporting surface defining one or more openings through which the measuring device performs the measuring of the web.

17. The apparatus of claim 16, wherein the measuring device is operable to measure the web property from only one side thereof.

18. A dry end of a tissue papermaking machine, comprising:

a dryer for drying a tissue paper web;

a reel-up positioned downstream of the dryer for winding the web to form a tissue paper roll;

a web support positioned between the dryer and the reel-up, the web support providing support to the web such that a first side of the web is exposed and an opposite second side of the web is in opposition to the web support, the web support providing support to the web from proximate the dryer substantially to the tissue paper roll; and a reflectance measuring device located proximate the first side of the web, the reflectance measuring device emitting measuring beams onto the web on the web support and receiving reflected measuring beams from the web and deducing at least one property of the web based on the reflected measuring beams.

19. The dry end of claim 18, wherein the web support comprises a fabric.

20. The dry end of claim 19, wherein the fabric forms a nip with the paper roll in the reel-up and guides the web into the nip.

21. A method for measuring a property of a traveling tissue paper web in a dry end of a tissue papermaking machine, the method comprising:

supporting the web on a web support located in the dry end between a dryer and a reel-up of the tissue papermaking machine such that a first side of the web is exposed and an opposite second side of the web is in opposition with the web support, the web support providing support to the web from proximate the dryer substantially to a tissue paper roll held in the reel-up;

emitting measuring beams onto the first side of the web on the web support so as to cause the measuring beams to be reflected from the web;

receiving the measuring beams reflected from the web; and analyzing the reflected measuring beams to measure a property of the paper.

22. The method of claim 21, wherein the web is supported on a traveling fabric during measurement of the web.

23. The method of claim 22, wherein the fabric comprises a through-air drying fabric, the fabric carrying the web through at least one through-air dryer, the fabric outside the through-air dryer carrying the web on an outward-facing surface of the fabric past a measuring station at which a reflectance measurement sensor is located for carrying out the emitting, receiving, and analyzing steps.

24. The method of claim 21, wherein the measuring beams are directed onto the web and received from the web at each of a plurality of fixed positions spaced apart in a cross-machine direction of the web so as to measure the web at a plurality of discrete spaced locations.

25. The method of claim 21, wherein the measuring beams are directed onto the web and received from the web by a traversing sensor that travels along a cross-machine direction of the web so as to measure the web across a width thereof.

26. A dry end of a papermaking machine, comprising:

a through-air dryer and a through-air drying fabric arranged in an endless loop that carries a paper web through the dryer, the endless loop of the fabric outside the dryer being arranged to carry the web on an outward-facing surface of the fabric past a measuring station; and at least one reflectance measurement sensor located at the measuring station, the sensor emitting measuring beams onto the web on the fabric and receiving reflected measuring beams from the web, and determining a property of the web based on the reflected measuring beams.

27. An apparatus for a dry end of a papermaking machine having a dryer for drying a paper web, the apparatus comprising:

a stabilizing foil for supporting and stabilizing the paper web exiting the dryer; and a measuring sensor for measuring one or more properties of the paper web downstream of the dryer, the measuring sensor being integrated into the foil, wherein the measuring sensor is traversable in a cross-machine direction for measuring properties of the paper web at various locations spaced apart in the cross-machine direction, the foil defining a slot therethrough extending in the cross-machine direction and the measuring sensor being aligned with the slot and traversable along the slot, and further comprising a movable cover for covering the slot when the measuring sensor is not being used.

* * * * *